United States Patent
Matheu et al.

(10) Patent No.: US 12,168,072 B2
(45) Date of Patent: Dec. 17, 2024

(54) OPTICALLY-INDUCED AUTO-ENCAPSULATION

(71) Applicant: Prellis Biologics, Inc., Hayward, CA (US)

(72) Inventors: Melanie P. Matheu, Hayward, CA (US); Erik Busby, Hayward, CA (US); Christopher Rogers, Hayward, CA (US); Milad Khorrami, Hayward, CA (US)

(73) Assignee: PRELLIS BIOLOGICS, INC., Hayward, CA (US)

( * ) Notice: Subject to any disclaimer, the term of this patent is extended or adjusted under 35 U.S.C. 154(b) by 609 days.

(21) Appl. No.: 17/163,091

(22) Filed: Jan. 29, 2021

(65) Prior Publication Data
US 2021/0361584 A1    Nov. 25, 2021

Related U.S. Application Data

(63) Continuation of application No. PCT/US2019/044243, filed on Jul. 30, 2019.
(Continued)

(51) Int. Cl.
*A61K 9/48* (2006.01)
*A61K 9/50* (2006.01)
*C08F 2/50* (2006.01)

(52) U.S. Cl.
CPC .......... *A61K 9/4833* (2013.01); *A61K 9/5089* (2013.01); *C08F 2/50* (2013.01)

(58) Field of Classification Search
CPC ........ A61K 9/4833; A61K 9/5089; C08F 2/50
See application file for complete search history.

(56) References Cited

U.S. PATENT DOCUMENTS

| | | |
|---|---|---|
| 4,669,812 A | 6/1987 | Hoebing |
| 5,024,508 A | 6/1991 | Horner et al. |

(Continued)

FOREIGN PATENT DOCUMENTS

| | | |
|---|---|---|
| CN | 203344507 U | 12/2013 |
| CN | 105176816 A | 12/2015 |

(Continued)

OTHER PUBLICATIONS

Allen et al. Imaging of Germinal Center Selection Events During Affinity Maturation. Science 315:528-531 (2007).
(Continued)

*Primary Examiner* — Emmanuel S Luk
*Assistant Examiner* — Elisa H Vera
(74) *Attorney, Agent, or Firm* — SQUIRE PATTON BOGGS (US) LLP

(57) ABSTRACT

The present disclosure provides methods and systems for optically-induced auto-encapsulation. A method of the present disclosure comprises providing a media chamber comprising a medium comprising (i) a three-dimensional (3D) object comprising a photo-emitter, (ii) at least one polymeric precursor, and (iii) a photoinitiator, and subjecting the medium in the media chamber to a stimulus (e.g., an energy beam or a chemical stimulus) to induce photo-emission from the photo-emitter to trigger the formation of a polymer matrix from the at least one polymeric precursor, which polymer matrix at least partially encapsulates the 3D object.

20 Claims, 5 Drawing Sheets

Related U.S. Application Data

(60) Provisional application No. 62/712,887, filed on Jul. 31, 2018.

(56) References Cited

U.S. PATENT DOCUMENTS

| | | | |
|---|---|---|---|
| 5,137,800 A * | 8/1992 | Neckers | G03F 7/0037 430/30 |
| 5,194,971 A | 3/1993 | Haines et al. | |
| 5,561,537 A | 10/1996 | Aritake et al. | |
| 6,139,574 A | 10/2000 | Vacanti et al. | |
| 6,259,450 B1 | 7/2001 | Chiabrera et al. | |
| 6,304,263 B1 | 10/2001 | Chiabrera et al. | |
| 6,608,228 B1 | 8/2003 | Cumpston et al. | |
| 6,819,469 B1 | 11/2004 | Koba | |
| 7,535,607 B2 | 5/2009 | Schwerdtner et al. | |
| 8,184,276 B2 | 5/2012 | Embry | |
| 8,339,695 B2 | 12/2012 | Haussler et al. | |
| 8,435,438 B1 | 5/2013 | Gross et al. | |
| 8,663,539 B1 | 3/2014 | Kolodziejska et al. | |
| 9,114,032 B1 | 8/2015 | Pulugurtha et al. | |
| 9,631,171 B2 | 4/2017 | Soman et al. | |
| 10,239,237 B1 | 3/2019 | Ensberg et al. | |
| 10,500,796 B1 | 12/2019 | Lazarovits | |
| 10,513,691 B2 | 12/2019 | Matheu et al. | |
| 10,933,579 B2 | 3/2021 | Matheu | |
| 2003/0090752 A1 | 5/2003 | Rosenberger et al. | |
| 2004/0067433 A1 | 4/2004 | Nirmal et al. | |
| 2004/0089804 A1 | 5/2004 | Dantus et al. | |
| 2004/0126694 A1 | 7/2004 | Devoe et al. | |
| 2004/0196524 A1 | 10/2004 | Hughes et al. | |
| 2004/0263930 A1 | 12/2004 | Payne et al. | |
| 2005/0208431 A1 | 9/2005 | Devoe et al. | |
| 2005/0226856 A1 | 10/2005 | Ahlfors et al. | |
| 2005/0286101 A1 | 12/2005 | Garner et al. | |
| 2006/0050340 A1 | 3/2006 | Schwerdtner et al. | |
| 2008/0194721 A1 | 8/2008 | Arney et al. | |
| 2008/0286482 A1 | 11/2008 | Cheung et al. | |
| 2009/0323508 A1 | 12/2009 | Tomura et al. | |
| 2010/0296148 A1 | 11/2010 | Reichelt et al. | |
| 2011/0033887 A1 | 2/2011 | Fang et al. | |
| 2011/0128555 A1 | 6/2011 | Rotschild et al. | |
| 2011/0149359 A1 | 6/2011 | Leister et al. | |
| 2011/0171689 A1 | 7/2011 | Warren et al. | |
| 2011/0254916 A1 | 10/2011 | Fan et al. | |
| 2011/0318528 A1 | 12/2011 | Cho et al. | |
| 2013/0012612 A1 | 1/2013 | Houbertz-Krauss et al. | |
| 2013/0203146 A1 | 8/2013 | Ying et al. | |
| 2013/0234372 A1 | 9/2013 | Almutairi et al. | |
| 2013/0304233 A1 | 11/2013 | Dean et al. | |
| 2014/0017651 A1 | 1/2014 | Sugimoto et al. | |
| 2014/0028663 A1 | 1/2014 | Smithwick et al. | |
| 2014/0113373 A1 | 4/2014 | Chien et al. | |
| 2014/0126029 A1 | 5/2014 | Fuetterer et al. | |
| 2014/0148880 A1 * | 5/2014 | Deisseroth | A61K 41/00 607/100 |
| 2015/0037445 A1 | 2/2015 | Murphy et al. | |
| 2015/0097315 A1 | 4/2015 | DeSimone et al. | |
| 2015/0165020 A1 | 6/2015 | Jaklenec et al. | |
| 2015/0217515 A1 | 8/2015 | Kim et al. | |
| 2015/0355379 A1 | 12/2015 | Wolter et al. | |
| 2015/0375453 A1 | 12/2015 | Yost et al. | |
| 2015/0375455 A1 | 12/2015 | Williams et al. | |
| 2016/0033874 A1 | 2/2016 | Tang et al. | |
| 2016/0107380 A1 | 4/2016 | Smoot et al. | |
| 2016/0282813 A1 | 9/2016 | Urbach | |
| 2016/0297131 A1 | 10/2016 | Kameoka et al. | |
| 2016/0298087 A1 | 10/2016 | Qu et al. | |
| 2016/0303797 A1 | 10/2016 | Moran | |
| 2016/0322560 A1 | 11/2016 | Sirbuly et al. | |
| 2017/0057162 A1 | 3/2017 | Spadaccini et al. | |
| 2017/0087766 A1 | 3/2017 | Chung et al. | |
| 2017/0120337 A1 | 5/2017 | Kanko et al. | |
| 2017/0136692 A1 | 5/2017 | Zheng et al. | |
| 2017/0281828 A1 | 10/2017 | Zhang et al. | |
| 2017/0283766 A1 | 10/2017 | Hribar et al. | |
| 2017/0348907 A1 | 12/2017 | Melde et al. | |
| 2017/0371248 A1 | 12/2017 | Tang et al. | |
| 2018/0002658 A1 * | 1/2018 | Miller | B29C 64/129 |
| 2018/0015672 A1 | 1/2018 | Shusteff et al. | |
| 2018/0117219 A1 | 5/2018 | Yang et al. | |
| 2018/0126630 A1 * | 5/2018 | Panzer | B29C 64/129 |
| 2018/0126671 A1 * | 5/2018 | Wilenski | B29C 64/118 |
| 2018/0147776 A1 | 5/2018 | Kotani et al. | |
| 2018/0188684 A1 | 7/2018 | Mullins | |
| 2018/0290384 A1 | 10/2018 | Hyde et al. | |
| 2018/0361666 A1 * | 12/2018 | Adzima | B29C 35/0888 |
| 2018/0370144 A1 | 12/2018 | Revanur et al. | |
| 2018/0371389 A1 | 12/2018 | Delrot et al. | |
| 2019/0016052 A1 | 1/2019 | Clark | |
| 2019/0031911 A1 | 1/2019 | Rolland et al. | |
| 2019/0111622 A1 | 4/2019 | Khalip | |
| 2020/0041957 A1 | 2/2020 | Mullins | |
| 2020/0063093 A1 | 2/2020 | Matheu et al. | |
| 2020/0080060 A1 | 3/2020 | Matheu et al. | |
| 2020/0255818 A1 * | 8/2020 | Knipe | C12N 11/089 |
| 2021/0187896 A1 * | 6/2021 | Price | B32B 27/08 |
| 2022/0025255 A1 * | 1/2022 | Congreve | B29C 64/165 |

FOREIGN PATENT DOCUMENTS

| | | |
|---|---|---|
| CN | 105574927 A | 5/2016 |
| CN | 105582571 A | 5/2016 |
| CN | 105877875 A | 8/2016 |
| CN | 106139244 A | 11/2016 |
| CN | 106163581 A | 11/2016 |
| CN | 105818383 B | 12/2017 |
| EP | 3018531 A1 | 5/2016 |
| EP | 3096171 A1 | 11/2016 |
| JP | H04267132 A | 9/1992 |
| WO | WO-2004034224 A2 | 4/2004 |
| WO | WO-2016083784 A1 | 6/2016 |
| WO | WO-2017181773 A1 | 10/2017 |
| WO | WO-2018165613 A1 | 9/2018 |
| WO | WO-2018218085 A2 | 11/2018 |
| WO | WO-2019051298 A1 | 3/2019 |
| WO | WO-2019186389 A1 | 10/2019 |
| WO | WO-2020028431 A1 | 2/2020 |
| WO | WO-2020028436 A1 | 2/2020 |
| WO | WO-2020102260 A1 | 5/2020 |
| WO | WO-2021062286 A1 | 4/2021 |
| WO | WO-2021146466 A1 | 7/2021 |

OTHER PUBLICATIONS

Bajaj et al. 3D Biofabrication Strategies for Tissue Engineering and Regenerative Medicine. Annu rev Biomed Eng 16:247-276 (2014).
Billiet et al. A review of trends and limitations in hydrogel-rapid prototyping for tissue engineering. Biomaterials 33:6020-6041 (2012).
Collins. Bioprinting is Changing Regenerative Medicine Forever. Stem Cells Dev 23 Suppl 1:79-82 (2014).
Cuchiara et al. Integration of Self-Assembled Microvascular Networks with Microfabricated PEG-Based Hydrogels. Adv Funct Mater 22(21):4511-4518 (2012 ).
Cui et al., 3D Bioprinting for Organ Regeneration, Adv Healthc Mater 6 (1):1-29 (2017).
Culver et al. Three-dimensional biomimetic patterning in hydrogels to guide cellular organization. Adv Mater 24(17):2344-2348 (2012).
Farsari et al. Two-photon polymerization of an Eosin Y-sensitized acrylate composite. Journal of Photochemistry and Photobiology A: Chemistry 181(1):132-135 (2006).
Hernandez et al. Three-dimensional spatiotemporal focusing of holographic patterns. Nat Commun 7:11928 (2016).
Huh et al. Reconstituting Organ-Level Lung Functions on a Chip. Science 328(5986): 1662-1668 (2010).
Itoh et al. Scaffold-Free Tubular Tissues Created by a Bio-3D Printer Undergo Remodeling and Endothelialization when Implanted in Rat Aortae. PLoS One 10(9):e0136681 (2015).
Jang et al. Human kidney proximal tubule-on-a-chip for drug transport and nephrotoxicity assessment. Integrative Biology 5(9):1089-1198 (2013).

(56) References Cited

OTHER PUBLICATIONS

King et al. 3D Proximal Tubule Tissues Recapitulate Key Aspects of Renal Physiology to Enable Nephrotoxicity Testing. Front Physiol 8:123 (2017).
Koo et al. Laser-assisted biofabrication in tissue engineering and regenerative medicine. J Mat Res 32(1):128-142 (2017).
Linnenberger. Live cell lithography and non-invasive mapping of neural networks. Univ of Colorado. Thesis (127 pgs) (2014).
Murphy et al. 3D bioprinting of tissues and organs. Nat Biotech 32:773-785 (2014).
Ovsianikov et al. Laser photofabrication of cell-containing hydrogel constructs. Langmuir 30:3787-3794 (2013).
PCT/US2018/021850 International Search Report and Written Opinion dated Jul. 24, 2018.
PCT/US2018034489 International Search Report and Written Opinion dated Jan. 17, 2019.
PCT/US2019/044238 International Search Report and Written Opinion dated Nov. 15, 2019.
PCT/US2019/044243 International Search Report and Written Opinion dated Nov. 19, 2019.
PCT/US2019/061035 International Search Report and Written Opinion dated Apr. 9, 2020.
PCT/US2020/052897 International Search Report and Written Opinion dated Jan. 13, 2021.
Pereira et al. 3D Photo-Fabrication for Tissue Engineering and Drug Delivery. Engineering 1(1):90-112 (2015).
Shusteff et al. Additive fabrication of 3D structures by holographic lithography/ In: Solid Freeform Fabrication 2016: Proceedings of the 27th Annual International Solid Freeform Fabrication Symposium—An additive Manufacturing Conference, Edited by Bourell, David L. et al., University of Texas, 2016, pp. 1183-1192.
Sistare et al. The Promise of New Technologies to Reduce, Refine, or Replace Animal Use while Reducing Risks of Drug Induced Liver Injury in Pharmaceutical Development. ILAR J 57(2):186-211 (2016).
Stankevicius et al. Holographic lithography for biomedical applications. Proc. of SPIE 8433:843312-1 to 843312-7 (May 11, 2012).
Suematsu et al. Generation of a synthetic lymphoid tissue-like organoid in mice. Nat Biotech 22(12):1539-1545 (2004).
Tas et al. Visualizing antibody affinity maturation in germinal centers. Science 10.1126/science.aad3439 (2016).
U.S. Appl. No. 15/925,582 Office Action dated Apr. 2, 2020.
U.S. Appl. No. 15/925,582 Office Action dated Jan. 11, 2019.
U.S. Appl. No. 15/925,582 Office Action dated Jun. 29, 2018.
U.S. Appl. No. 15/925,582 Office Action dated Sep. 5, 2019.
U.S. Appl. No. 16/044,413 Office Action dated Apr. 4, 2019.
U.S. Appl. No. 16/669,439 Office Action dated Jan. 24, 2020.
U.S. Appl. No. 16/669,439 Office Action dated Jul. 16, 2020.
Yanagawa et al. Hydrogel microfabrication technology toward three dimensional tissue engineering. Regenerative Therapy 3:45-57 (2016).
Yuan et al. Laser Scanning Holographic Lithography for Flexible 3D Fabrication of Multi-Scale Integrated Nano-structures and Optical Biosensors. Sci Rep 6:22294 (2016).
Zhang et al. Optimized holographic femtosecond laser patterning method towards rapid integration of high-quality functional devices in microchannels. Sci Rep 6:33281 (2016).
Zheren et al. 3D Micro-concrete Hybrid Structures Fabricated by Femtosecond Laser Two-Photon Polymerization for Biomedical and Photonic Applications. 2016 IEEE International Conference on Industrial Technology (ICIT), Taipei, Taiwan (pp. 1108-1114) (2016).
Zhu et al. Direct 3D bioprinting of prevascularized tissue constructs with complex microarchitecture. Biomaterials 124:106-115 (2017).
PCT/US2021/013494 International Search Report and Written Opinion dated May 12, 2021.

* cited by examiner

|   | Chemical name | Full name | Lot number | Manufacturer | Concentration | Amount for making 1455μl J0 formulation |
|---|---|---|---|---|---|---|
| 1 | PEGda700 (>99.9%) | Poly(ethylene glycol) diacrylate-Mn700 | 455008-500ML | Sigma-Aldrich | 82.5 vol% | 1200 μl |
| 2 | 1X PBS | Phosphate buffered saline | - | - | 14 vol% | 195 μl |
| 3 | TEA (>99.9%) | Triethylamine | 90279-100ML | Sigma-Aldrich | 1 vol% | 15 μl |
| 4 | NPG (25mM) | N-Phenylglycine | 330469 | Sigma-Aldrich | 0.26 mM | 15 μl |
| 5 | GSH (77mg/ml) | Glutathione | 78259 | Thermo Scientific | 2.56 mM | 15 μl |
| 6 | NVP | 1-Vinyl-2-pyrrolidinone | V3409 | Sigma-Aldrich | 96.47 mM | 15 μl |
| 7 | Eosin (2 wt%) | Eosin Y (Disodium Salt) | 154354 | Thermo Scientific | Depends on structure | Depends on structure |

FIG. 3

| NVP concentration | Exposure Frequency (EF) | Printing time for a basket |
|---|---|---|
| 0 | 30 Hz | 79 min |
| 0 | 40 Hz | No print |
| 1 vol% | 30 Hz | 79 min |
| 1 vol % | 40 Hz | 57 min |
| 1 vol% | 50 Hz | No print |

OPTICALLY-INDUCED AUTO-ENCAPSULATION

CROSS-REFERENCE

This application is a continuation of International Application No. PCT/US2019/044243, filed on Jul. 30, 2019, which claims the benefit of U.S. Provisional Application No. 62/712,887, filed Jul. 31, 2018, Entitled: "Optically-Induced Auto-Encapsulation," the contents of each are incorporated herein by reference in their entirety.

BACKGROUND

The present disclosure provides methods and systems comprising the use of energy (e.g., high intensity light or laser) that may be either pulsed or continuous to induce fluorescence of a three-dimensional (3D) biological material at a specific wavelength such that it is reactive with a given medium. In some cases, the medium solidifies locally in a non-directed manner due to the non-directional fluorescence emission from the 3D biological material.

SUMMARY

The present disclosure provides methods and systems for optically-induced (e.g, fluorescently-induced) auto-encapsulation. Methods and systems of the present disclosure may operate under a number of fundamental concepts, including, without limitation, holography and multi-photon absorption. Multi-photon absorption is a process wherein multiple photons are absorbed effectively and simultaneously as if they were a single photon of an energy equal to the sum of the energy of the individual photons. Most commonly, two near-infrared photons (e.g., about 1.2 electron volts (eV)) can be absorbed as if they were a single visible (e.g., about 2.4 eV) photon.

For this process to occur, a high density of photons may be required to occupy a volume simultaneously. As a result, short pulse lasers with very high peak powers may be used to induce multiphoton absorption events. Additionally, this high density of photons may occur within an absorbing material with properties that allow for the multi-photon absorption event to occur. If a material is not inherently well suited for this, the incorporation of a molecular or nanoparticulate dye may sensitize an otherwise unabsorbing material.

In an aspect, the present disclosure provides a method for encapsulating a three-dimensional (3D) object, comprising: (a) providing a media chamber comprising a medium comprising (i) the 3D object comprising a photo-emitter, (ii) at least one polymeric precursor, and (iii) a photoinitiator; and (b) directing at least one energy beam to the medium in the media chamber to induce photo-emission from the photo-emitter wherein the photo-emitter emits energy that triggers the photoinitiator to initiate formation of a polymer matrix from the at least one polymeric precursor, which polymer matrix at least partially encapsulates the 3D object.

In some embodiments, the photo-emitter contains one or more emissive components. In some embodiments, the photo-emitter is a fluorescent polymer sphere. In some embodiments, the photo-emitter is a cell-containing emissive nanoparticle. In some embodiments, the medium further comprises a photoinhibitor that prevents formation of the polymer matrix in one or more selected locations of the medium. In some embodiments, the at least one energy beam comprises a single wavelength. In some embodiments, the at least one energy beam comprises a plurality of wavelengths.

In some embodiments, the method further comprises using a full spectrum illumination with distinct wavelength bands blocked. In some embodiments, the method further comprises using a full spectrum illumination. In some embodiments, the at least one energy beam is selected from the group consisting of a laser, a light emitting diode, an arc lamp, an incandescent light source, and a fluorescent light source. In some embodiments, the 3D object comprising the photo-emitter is selected from the group consisting of a cell comprising the photo-emitter, a particle comprising the photo-emitter, a microparticle comprising the photo-emitter, a nanoparticle comprising the photo-emitter, and a surface comprising the photo-emitter. In some embodiments, the cell is selected from the group consisting of endothelial cells, fibroblasts, immune cells, keratinocytes, melanocytes, kidney cells, hepatocytes and cardiomyocytes.

In some embodiments, the photo-emitter is selected from the group consisting of a chemiluminescent component, a photoluminescent component, a fluorescent molecule, a phosphorescent molecule, a luminescent molecule, a nanoparticle, a quantum dot particle, a microparticle, a histological stain, an immunofluorescent dye, a fluorescent dye, and a fluorescent protein. In some embodiments, the photo-emitter is selected from the group consisting of a photo-emitting peptide, a photo-emitting cell penetrating peptide, a photo-emitting intracellular probe, a photo-emitting reporter, and a photo-emitting activity-based reporter. In some embodiments, the 3D object comprises at least two photo-emitters. In some embodiments, the 3D object comprises a fluorescence resonance energy transfer (FRET) reporter.

In some embodiments, the photoinitiator is selected from the group consisting of Eosin Y, erythrosine, rose Bengal, xanthone derivatives, triethanolamine, azobisisobutyronitrile (AIBN), benzoin derivatives, benziketals, hydroxyalkylphenones, acetophenone derivatives, trimethylolpropane triacrylate (TPT), acryloyl, chloride, benzoyl peroxide, camphorquinone, benzophenone, thioxanthones, and 2-hydroxy-1-[4-(hydroxyethoxy)phenyl]-2-methyl-1-propanone, 4-(2-hydroxyethylethoxy)-phenyl-(2-hydroxy-2-methyl propyl) ketone, 1-hydroxycyclohexyl-1-phenyl ketone and 2,2-dimethoxy-2-phenylacetophenone, and lithium phenyl-2,4,6-trimethylbenzoylphosphinate (LAP). In some embodiments, the at least one polymeric precursor is selected from the group consisting of collagen, gelatin, chitosan, polyethylene glycol (PEG), and polylactic-co-glycolic acid (PLGA), vinyl alcohol derivatives, vinylpyrrolidone derivatives, acrylate derivatives, methacrylate derivatives, and styrene derivatives.

In some embodiments, the media chamber further comprises a three-dimensional (3D) object, wherein the 3D object does not contain a photo-emitter. In some embodiments, the medium comprises more than one 3D object comprising a photo-emitter. In some embodiments, the more than one 3D object comprises a photo-emitter that does not have overlapping excitation wavelengths with another 3D object comprising a photo-emitter. In some embodiments, the method further comprises differentiating different 3D object types based on the formation of the polymer matrix from the at least one polymeric precursor. In some embodiments, the method further comprises separating out from the medium any of the 3D objects without resultant encapsulation by the polymer matrix. In some embodiments, the 3D objects are separated using a method comprising the group consisting of separation by physical size, separation by chemical binding, separation by electrostatic forces, separation by magnetic interactions, separation by mass, and separation by solubility.

Another aspect of the present disclosure provides a method for encapsulating a three-dimensional (3D) objects, comprising: (a) providing a media chamber comprising a medium comprising (i) the 3D object comprising a photo-emitter, (ii) at least one polymeric precursor, and (iii) a photoinitiator; and (b) applying a chemical stimulus to the medium in the media chamber to induce photo-emission from the photo-emitter, wherein the photo-emitter emits energy that triggers the photoinitiator to initiate formation of a polymer matrix from the at least one polymeric precursor, which polymer matrix at least partially encapsulates the 3D object.

In some embodiments, the medium further comprises a photoinhibitor that prevents formation of the polymer matrix in one or more selected locations of the medium. In some embodiments, the 3D object comprising the photo-emitter is selected from the group consisting of a cell comprising the photo-emitter, a particle comprising the photo-emitter, a microparticle comprising the photo-emitter, a nanoparticle comprising the photo-emitter, and a surface comprising the photo-emitter. In some embodiments, the cell is selected from the group consisting of endothelial cells, fibroblasts, immune cells, keratinocytes, melanocytes, kidney cells, hepatocytes and cardiomyocytes.

In some embodiments, the photo-emitter is selected from the group consisting of a chemiluminescent component, a photoluminescent component, a fluorescent molecule, a phosphorescent molecule, a luminescent molecule, a nanoparticle, a quantum dot particle, a microparticle, a histological stain, an immunofluorescent dye, a fluorescent dye, and a fluorescent protein. In some embodiments, the photo-emitter is selected from the group consisting of a photo-emitting peptide, a photo-emitting cell penetrating peptide, a photo-emitting intracellular probe, a photo-emitting reporter, and a photo-emitting activity-based reporter. In some embodiments, the 3D object comprises at least two photo-emitters. In some embodiments, the 3D object comprises a fluorescence resonance energy transfer (FRET) reporter.

In some embodiments, the photoinitiator is selected from the group consisting of Eosin Y, erythrosine, rose Bengal, xanthone derivatives, triethanolamine, azobisisobutyronitrile (AIBN), benzoin derivatives, benziketals, hydroxyalkylphenones, acetophenone derivatives, trimethylolpropane triacrylate (TPT), acryloyl, chloride, benzoyl peroxide, camphorquinone, benzophenone, thioxanthones, and 2-hydroxy-1-[4-(hydroxyethoxy)phenyl]-2-methyl-1-propanone, 4-(2-hydroxyethylethoxy)-phenyl-(2-hydroxy-2-methyl propyl) ketone, 1-hydroxycyclohexyl-1-phenyl ketone and 2,2-dimethoxy-2-phenylacetophenone, and lithium phenyl-2,4,6-trimethylbenzoylphosphinate (LAP).

In some embodiments, the at least one polymeric precursor is selected from the group consisting of collagen, gelatin, chitosan, polyethylene glycol (PEG), and polylactic-co-glycolic acid (PLGA), vinyl alcohol derivatives, vinylpyrolidone derivatives, acrylate derivatives, methacrylate derivatives, and styrene derivatives. In some embodiments, the media chamber further comprises a three-dimensional (3D) object, wherein the 3D object does not contain a photo-emitter. In some embodiments, the medium comprises more than one 3D object comprising a photo-emitter. In some embodiments, the more than one 3D object comprises a photo-emitter that does not have overlapping excitation wavelengths with another 3D object comprising a photo-emitter.

In some embodiments, the method further comprises differentiating different 3D object types based on the formation of the polymer matrix from the at least one polymeric precursor. In some embodiments, the method further comprises separating out from the medium any of the 3D objects without resultant encapsulation by the polymer matrix. In some embodiments, the 3D objects are separated using a method comprising the group consisting of separation by physical size, separation by chemical binding, separation by electrostatic forces, separation by magnetic interactions, separation by mass, and separation by solubility.

In some embodiments, the chemical stimulus is selected from the group consisting of heat, electrical stimulus, magnetic stimulus, and combinations thereof.

Another aspect of the present disclosure provides a system for encapsulating a three-dimensional (3D) object, comprising: a media chamber configured to contain a medium comprising (i) the 3D object comprising a photo-emitter, (ii) at least one polymeric precursor, and (iii) a photoinitiator; at least one energy source configured to direct at least one energy beam to the media chamber; and one or more computer processors operatively coupled to the at least one energy source, wherein the one or more computer processors are individually or collectively programmed to direct the at least one energy source to the medium in the media chamber to induce a photo-emission from the photo-emitter, wherein the photo-emitter emits energy that is sufficient to trigger the photoinitiator to initiate formation of a polymer matrix from the at least one polymeric precursor, which the polymer matrix at least partially encapsulates the 3D object.

In some embodiments, the medium further comprises a photoinhibitor that prevents formation of the polymer matrix in one or more selected locations of the medium. In some embodiments, the at least one energy beam comprises a single wavelength. In some embodiments, the at least one energy beam comprises a plurality of wavelengths. In some embodiments, the one or more computer processors are individually or collectively programmed to use full spectrum illumination with distinct wavelength bands blocked. In some embodiments, the one or more computer processors are individually or collectively programmed to use a full spectrum illumination.

In some embodiments, the at least one energy beam is selected from the group consisting of a laser, a light emitting diode, arc lamp, incandescent, and a fluorescent light source. In some embodiments, the 3D object comprising the photo-emitter is a cell comprising the photo-emitter, a particle comprising the photo-emitter, a microparticle comprising the photo-emitter, a nanoparticle comprising the photo-emitter, or a surface comprising the photo-emitter. In some embodiments, the cell is selected from the group consisting of endothelial cells, fibroblasts, immune cells, keratinocytes, melanocytes, kidney cells, hepatocytes and cardiomyocytes.

In some embodiments, the photo-emitter is selected from the group consisting of a chemiluminescent component, a photoluminescent component, a fluorescent molecule, a phosphorescent molecule, a luminescent molecule, a nanoparticle, a quantum dot particle, a microparticle, a histological stain, an immunofluorescent dye, a fluorescent dye, and a fluorescent protein. In some embodiments, the photo-emitter is selected from the group consisting of a photo-emitting peptide, a photo-emitting cell penetrating peptide, a photo-emitting intracellular probe, a photo-emitting reporter, and a photo-emitting activity based reporter. In some embodiments, the 3D object comprises at least two photo-emitters. In some embodiments, the 3D object comprises a fluorescence resonance energy transfer (FRET) reporter.

In some embodiments, the photoinitiator is selected from the group consisting of Eosin Y, erythrosine, rose Bengal, xanthone derivatives, triethanolamine, azobisisobutyronitrile (AIBN), benzoin derivatives, benziketals, hydroxyalkylphenones, acetophenone derivatives, trimethylolpropane triacrylate (TPT), acryloyl, chloride, benzoyl peroxide, camphorquinone, benzophenone, thioxanthones, and 2-hydroxy-1-[4-(hydroxyethoxy)phenyl]-2-methyl-1-propanone, 4-(2-hydroxyethylethoxy)-phenyl-(2-hydroxy-2-methyl propyl) ketone, 1-hydroxycyclohexyl-1-phenyl ketone and 2,2-dimethoxy-2-phenylacetophenone, and lithium phenyl-2,4,6-trimethylbenzoylphosphinate (LAP).

In some embodiments, the at least one polymeric precursor is selected from the group consisting of collagen, gelatin, chitosan, polyethylene glycol (PEG), polylactic-co-glycolic acid (PLGA), vinyl alcohol derivatives, vinylpyrrolidone derivatives, acrylate derivatives, methacrylate derivatives, and styrene derivatives. In some embodiments, the media chamber further comprises a three-dimensional (3D) object that does not contain a photo-emitter. In some embodiments, the medium comprises more than one 3D object comprising a photo-emitter. In some embodiments, the more than one 3D object comprises a photo-emitter that does not have overlapping excitation wavelengths with another 3D object comprising a photo-emitter.

In some embodiments, the one or more computer processors are individually or collectively programmed to differentiate different 3D object types based on the formation of the polymer matrix from the at least one polymeric precursor, without resultant encapsulation by the polymer matrix. In some embodiments, the differentiation is selected from the group consisting of separation by physical size, separation by chemical binding, separation by electrostatic forces, separation by magnetic interactions, separation by mass, and separation by solubility.

Another aspect of the present disclosure provides a system for encapsulating a three-dimensional (3D) objects, comprising: a media chamber configured to contain a medium comprising (i) the 3D object comprising a photo-emitter, (ii) at least one polymeric precursor, and (iii) a photoinitiator; at least one source configured to apply a chemical stimulus to the media chamber; and one or more computer processors operatively coupled to the at least one source, wherein the one or more computer processors are individually or collectively programmed to apply the chemical stimulus to the medium in the media chamber to induce a photo-emission from the photo-emitter, wherein the photo-emitter emits energy that is sufficient to trigger the photoinitiator to initiate formation of a polymer matrix from the at least one polymeric precursor, which the polymer matrix at least partially encapsulates the 3D object.

In some embodiments, the medium further comprises a photoinhibitor that prevents formation of the polymer matrix in one or more selected locations of the medium. In some embodiments, the 3D object comprising the photo-emitter is selected from the group consisting of a cell comprising the photo-emitter, a particle comprising the photo-emitter, a microparticle comprising the photo-emitter, a nanoparticle comprising the photo-emitter, and a surface comprising the photo-emitter. In some embodiments, the cell is selected from the group consisting of endothelial cells, fibroblasts, immune cells, keratinocytes, melanocytes, kidney cells, hepatocytes and cardiomyocytes.

In some embodiments, the photo-emitter is selected from the group consisting of a chemiluminescent component, a photoluminescent component, a fluorescent molecule, a phosphorescent molecule, a luminescent molecule, a nanoparticle, a quantum dot particle, a microparticle, a histological stain, an immunofluorescent dye, a fluorescent dye, and a fluorescent protein. In some embodiments, the photo-emitter is selected from the group consisting of a photo-emitting peptide, a photo-emitting cell penetrating peptide, a photo-emitting intracellular probe, a photo-emitting reporter, and a photo-emitting activity based reporter.

In some embodiments, the 3D object comprises at least two photo-emitters. In some embodiments, the 3D object comprises a fluorescence resonance energy transfer (FRET) reporter. In some embodiments, the photoinitiator is selected from the group consisting of Eosin Y, erythrosine, rose Bengal, xanthone derivatives, triethanolamine, azobisisobutyronitrile (AIBN), benzoin derivatives, benziketals, hydroxyalkylphenones, acetophenone derivatives, trimethylolpropane triacrylate (TPT), acryloyl, chloride, benzoyl peroxide, camphorquinone, benzophenone, thioxanthones, and 2-hydroxy-1-[4-(hydroxyethoxy)phenyl]-2-methyl-1-propanone, 4-(2-hydroxyethylethoxy)-phenyl-(2-hydroxy-2-methyl propyl) ketone, 1-hydroxycyclohexyl-1-phenyl ketone and 2,2-dimethoxy-2-phenylacetophenone, and lithium phenyl-2,4,6-trimethylbenzoylphosphinate (LAP). In some embodiments, the at least one polymeric precursor is selected from the group consisting of collagen, gelatin, chitosan, polyethylene glycol (PEG), and polylactic-co-glycolic acid (PLGA), vinyl alcohol derivatives, vinylpyrrolidone derivatives, acrylate derivatives, methacrylate derivatives, and styrene derivatives.

In some embodiments, the media chamber further comprises a three-dimensional (3D) object which does not contain a photo-emitter. In some embodiments, the medium comprises more than one 3D object comprising a photo-emitter. In some embodiments, the more than one 3D object comprises a photo-emitter that does not have overlapping excitation wavelengths with another 3D object comprising a photo-emitter. In some embodiments, the one or more computer processors are individually or collectively programmed to differentiate different 3D object types based on the formation of the polymer matrix from the at least one polymeric precursor. In some embodiments, the one or more computer processors are individually or collectively programmed to separate out from the medium any of the 3D objects without resultant encapsulation by the polymer matrix. In some embodiments, the separation is selected from the group consisting of the separation by physical size, separation by chemical binding, separation by electrostatic forces, separation by magnetic interactions, separation by mass, and separation by solubility.

In some embodiments, the chemical stimulus is selected from the group consisting of heat, electrical stimulus, magnetic stimulus, and combinations thereof.

Another aspect of the present disclosure provides a method for encapsulating a three-dimensional (3D) object, comprising: (a) providing a media chamber comprising a medium comprising (i) said three-dimensional (3D) object comprising a photo-emitter, (ii) at least one polymeric precursor, and (iii) a photoinitiator; and (b) directing a stimulus to said medium in said media chamber sufficient to induce photo-emission from said photo-emitter, such that said photo-emitter emits energy that triggers said photoinitiator to initiate formation of a polymer matrix from said at least one polymeric precursor, which polymer matrix at least partially encapsulates said 3D object.

Another aspect of the present disclosure provides a method for encapsulating a three-dimensional (3D) object, comprising stimulating a photo-emitter coupled to said 3D object to emit energy that triggers a photoinitiator in proximity to said 3D object to initiate formation of a polymer matrix that at least partially encapsulates said 3D object.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 3 shows example formulations of example chemicals that may be used in a resin in the methods of the present disclosure.

DETAILED DESCRIPTION

Figure 1A:
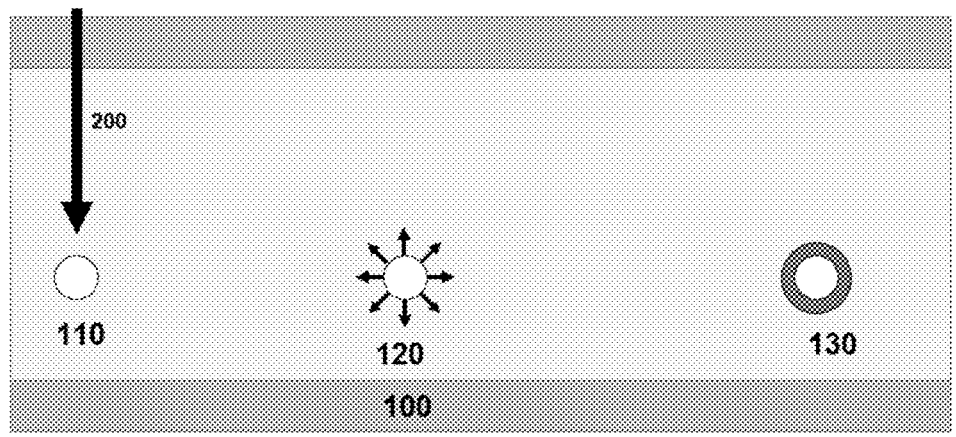
FIG. 1A schematically represents the cell encapsulation process and an example apparatus.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The terminology used herein is for the purpose of describing particular cases only and is not intended to be limiting. As used herein, the singular forms "a," "an" and "the" are intended to include the plural forms as well, unless the context clearly indicates otherwise. Furthermore, to the extent that the terms "including," "includes," "having" "has," "with," or variants thereof are used in either the detailed description and/or the claims, such terms are intended to be inclusive in a manner similar to the term "comprising."

The term "about" or "approximately" refers to an amount that is near the stated amount by about 10%, 5%, or 1%, including increments therein. For example, "about" or "approximately" can mean a range including the particular value and ranging from 10% below that particular value and spanning to 10% above that particular value.

The term "biological material," as used herein, generally refers to any material that may serve a chemical or biological function. The biological material may include a cell or multiple cells. The cells may be of the same type or different types. Biological material may be biologically functional tissue or functional tissue, which may be a biological structure that is capable of serving, or serving, a biomechanical or biological function. Biologically functional tissue may comprise cells that are within diffusion distance from each other, comprises at least one cell type wherein each cell is within diffusion distance of a capillary or vascular network component, facilitates and/or inhibits the fulfillment of protein function, or any combination thereof. Biologically functional tissue may be at least a portion of tissue or an organ, such as a vital organ. In some examples, the biological material may be used for drug development, such as, for example, screening multiple cells or tissue with different therapeutic agents.

Biological material may include a matrix, such as a polymeric matrix, including one or more other types of material, such as cells. Biological material may be in various shapes, sizes or configurations. In some instances, biological material may be consumable by a subject (e.g., an animal), such as meat or meat-like material. The biological material may include macromolecules, such as polypeptides and/or protein.

The term "energy beam," as used herein, generally refers to a beam of energy. The energy beam may be a beam of electromagnetic energy or electromagnetic radiation. The energy beam may be a particle beam. An energy beam may be a light beam (e.g., gamma waves, x-ray, ultraviolet, visible light, infrared light, microwaves, or radio waves).

The light beam may be a coherent light beam, as may be provided by light amplification by stimulated emission of radiation ("laser"). In some examples, the light beam is generated by a laser diode or a multiple diode laser.

Multiphoton absorption may result in unique optical behavior, namely confinement of absorption to only the most intense portion of the focus of a beam. For example, focusing light into a single photon absorbing material results in an absorption profile resembling an hour glass that extends throughout the entirety of the material thickness. In contrast, light focused into a multi-photon absorbing material may result in an absorption profile resembling a small ellipsoid centered at the focal point of the beam. Multiphoton absorbing materials may be selected to be transparent at the wavelength of the excitation laser, e.g., a near-infrared two photon dye which is transparent in the near-infrared spectra region and absorbing in the visible spectral region. This may allow for the excitation light to penetrate deeper into the material than may be possible with single photon techniques because the light may only be absorbed at the focal point.

The combined advantages of excitation confinement and high optical transmissivity have made multi-photon optical techniques popular within bioscience imaging communities, where the technique has been applied to conduct high-resolution and deep tissue imaging of cells and tissues. Additionally, this technique has been applied to nano- and micro-fabrication using two-photon lithography (TPL). The aforementioned excitation confinement allows TPL to accomplish direct laser writing (DLW) fabrication of 3-dimensional objects with resolution on the order of one micron. While powerful, this technique may be limited to exposure of one voxel (the three-dimensional equivalent of a pixel) at a time. This, if combined with beam steering hardware limitations and the exposure (dwell) time requirements of the utilized photosensitive material, may place an upper limit on the speed of a single-point exposure system. Compared to the scanning of a single focal point in traditional direct laser writing, holographic exposure may provide significant improvement in speed without significantly impacting the resolution of the technique.

Auto-encapsulation of a cell or a particle may be employed with numerous types of energy beams including coherent lasers that produce single photon absorption or bright light tuned to a given wavelength, spectral set, entire visible spectrum, ultraviolet (UV) light, or infrared (IR) light.

Auto-encapsulation of cells, particles, or biologically active materials may occur with broad exposure of the system or with spatial pin-point emission in three-dimensions as driven and determined by feedback to the holographic spatial light modulators (SLMs). Thus, spatial pin-point emission in 3D may allow for specific illumination and selection that may or may not be based on additional parameters, such as size or morphology of the cell, particle, or unit of interest.

Conceptually, holography is the optical projection of a three-dimensional image or "hologram." Applied to multi-photon lithography, holography may allow for the exposure of many voxels simultaneously and the facile fabrication of complex objects. Benefits to this approach relative to single-point exposure DLW, include, but are not limited to print speed. Because many voxels may be exposed simultaneously, the print speed limit imposed by the dwell time of the print medium may no longer be a practical limit on the print speed of the system. Additionally, holography may allow for printing of two- and three-dimensional objects or object fragments in a single exposure.

Hologram projection may be accomplished through modulating the phase and/or amplitude of a laser beam, such as by an electronically addressable optical modulator (e.g., a spatial light modulator (SLM)), then via Fourier optics using the modulated beam to expose the print medium. The SLM may be a device with electronically addressable pixels that, in typical configurations, may impart a variable phase delay to the impinging beam by electronically controlling the orientation of a liquid crystal. This variable phase delay may be controlled with an external computer to allow for the beam to be rapidly and precisely controlled. Depending on the imposed phase delay, the beam may be steered, focused, defocused, or arbitrarily shaped. The resultant phase profile can then be Fourier conjugated to transform the frequency-spatial domain profile imparted by the SLM into a spatial domain hologram projected into the intended print medium. This may be done by imaging the SLM phase profile (with the appropriate magnification/demagnification) onto the back aperture of a microscope objective.

Within this lithographic framework, the pattern displayed on the SLM may determine the projected image and, therefore, the object that may form in the print field of the system. The displayed SLM image may be the spatial-frequency domain image of the intended object print. Conceptually, this may be similar to the Fourier transform of the target projected image. Quantitatively, optimization beyond simple Fourier transform may be necessary. Most commonly, the Gerchburg-Saxton algorithm may be used to calculate holograms, though there are a number of other algorithms capable of synthesizing holograms.

In an aspect, the present disclosure provides a method of optically-induced (e.g., fluorescent-induced) auto-encapsulation of at least one cell. The method may comprise: labeling the at least one cell with a fluorescent label to generate at least one labeled cell; contacting the at least one labeled cell with a medium comprising one or more precursors and a photoinitiator; and directing at least one energy beam into the medium to initiate a photo-polymerization reaction in the medium directly surrounding the at least one labeled cell to generate an auto-encapsulation of the at least one labeled cell.

The at least one energy beam may comprise a single wavelength. The at least one energy beam may comprise multiple distinct wavelengths. The method may further comprise using a full spectrum illumination with distinct wavelength bands blocked. The method may further comprise using a full spectrum illumination. The at least one energy beam may be a coherent multi-photon laser beam, a coherent single-photon laser beam, a light emitting diode (LED)-based beam, or any other suitable energy beam.

In an aspect, the present disclosure provides a method of fluorescent-induced auto-encapsulation of at least one entity. The method may comprise: contacting the at least one entity with a medium comprising one or more precursors and a photoinitiator; and directing at least one energy beam into the medium to initiate a photo-polymerization reaction in the medium directly surrounding the at least one entity to generate an auto-encapsulation of the at least one entity.

The entity may fluoresce in response to a given wavelength. The entity may be a particle. The entity may be a nanoparticle. The entity may be a cell. The entity may be labeled with a dye. The entity may be a nanoparticle element or a fluorescent element. The at least one energy beam may comprise a single wavelength. The at least one energy beam may comprise multiple distinct wavelengths. The method may further comprise using a full spectrum illumination with distinct wavelength bands blocked. The method may further comprise using a full spectrum illumination. The at least one energy beam may be a coherent multi-photon laser beam, a coherent single-photon laser beam, a light emitting diode (LED)-based beam, or any other suitable energy beam.

The present disclosure provides a method of encapsulating three-dimensional (3D) objects. The method may comprise providing a media chamber (e.g., a container). The media chamber may comprise a medium. The medium may comprise a three-dimensional (3D) object. The 3D object may comprise a photo-emitter, at least one polymeric precursor, and at least a photoinitiator.

The method may comprise applying a chemical stimulus to the medium in the media chamber. The chemical stimulus may cause a chemical reaction. The chemical reaction may induce photo-emission from the photo-emitter. Chemical stimulus may comprise directing at least one energy beam to the medium in the media chamber such that energy from the at least one energy beam may excite the photo-emitter. In some cases, the chemical stimulus may be heat. In some cases, the chemical stimulus may be an electrical stimulus. In some cases, the chemical stimulus may be a magnetic stimulus. Various types of energy may be used. Various types of chemical and physical and/or combinations thereof may be used.

The chemical stimulus may be provided by a light source. The chemical source may comprise light. The method may comprise directing at least one energy beam to the medium in the media chamber such that energy from the at least one energy beam may excite the photo-emitter.

Upon ensuing the chemical reaction, the photo-emitter may emit energy that may trigger the photoinitiator that may initiate formation of a polymer matrix from the at least one polymeric precursor. The polymer matrix may at least partially encapsulate the 3D object.

In some cases, the medium may comprise a photoinhibitor that may prevent formation of the polymer matrix in one or more selected locations of the medium.

In some cases, the at least one energy beam may comprise a single wavelength. In some cases, the at least one energy beam may comprise a plurality of wavelengths. A plurality of wavelengths may be at least 1, 2, 3, 4, 5, 6, 7, 8, 9, 10, 11, 12, 13, 14, 15, 16, 17, 18, 19, 20, or more wavelengths. The number of wavelengths is not meant to be limiting.

The method may further comprise using a full spectrum illumination with distinct wavelength bands blocked. The method may further comprise using a full spectrum illumination. The method may further comprise using a full spectrum illumination without blocking distinct wavelength bands.

In some cases, the at least one energy beam may be provided by a light source. Light source may be a laser, a light emitting diode, an arc lamp, an incandescent, or a fluorescent light source.

In some cases the 3D object may be auto-fluorescent. In some cases, the 3D object may be emissive. In some cases, the 3D object may be photo-inert. In some cases, the 3D object, which by itself, may be photo-inert may comprise a photo-emitter, a photo-emitting object, such as a label, a tag, a fluorescent component, an otherwise emissive component, or more. For example, in some cases the methods may comprise using a fluorescent polymer 3D shape, such as for example, a fluorescent polymer sphere. In another example, the method may comprise a cell containing emissive nanoparticles.

In some cases, the 3D object may be a cell. The cell may comprise a photo-emitter. The cell may be auto-fluorescent. The cell may be a genetically modified fluorescent cell, such as for example a green fluorescent protein (GFP) HeLa cell, or other type of fluorescent cell comprising a photo-emitter of any kind.

The photo-emitter may be a particle. The particle may emit light. The particle may be a photo-emitter. The photo-emitter may be a microparticle, a nanoparticle comprising, or a surface. Photo-emitters may emit light via various different mechanisms. The type of photo-emitter may not be limiting.

In some cases, the cells may be from the group consisting of endothelial cells, fibroblasts, immune cells, keratinocytes, melanocytes, kidney cells, hepatocytes and cardiomyocytes.

Cells may be healthy cells or diseased cells, such as cells from various tissues. Non-limiting examples may comprise cancer cells. Cells may be from the nervous system, the cardiovascular system, and more.

The methods and systems may comprise providing a media chamber. The media chamber may comprise cells. The media chamber may be configured to contain a medium comprising a plurality of cells. The cells may comprise one type of cells. The cells may comprise at least 1, 2, 3, 4, 5, 6, 7, or more types of cells. The cells may be any type of cells. The cells may be adherent or suspension cells. The cells may be healthy or diseased cells. The cells may be cancer cells. The cells may be stem cells.

The medium may comprise one or more precursors. Precursors may be polymer precursors. The medium may comprise polymerizable material. The medium may comprise various chemicals. Chemicals may be present at varying ratios. Such ratios may be adjusted and optimized for specific purposes and applications.

In some cases, different types of cells may be co-cultured in the polymerizable material. The polymerizable material may be suitable for growing cells. The polymerizable material may be biocompatible.

Cells may comprise endothelial cells, microvascular endothelial cells, pericytes, smooth muscle cells, fibroblasts, endothelial progenitor cells, lymph cells, T-cells such as helper T-cells and cytotoxic T-cells, B-cells, natural killer (NK) cells, reticular cells, hepatocytes, or any combination thereof. The first cell group and/or second cell group may comprise exocrine secretory epithelial cells, hormone-secreting cells, epithelial cells, nerve cells, adipocytes, kidney cells, pancreatic cells, pulmonary cells, extracellular matrix cells, muscle cells, blood cells, immune cells, germ cells, interstitial cells, or any combination thereof Cells may comprise exocrine secretory epithelial cells including but not limited to salivary gland mucous cells, mammary gland cells, sweat gland cells such as eccrine sweat gland cell and apocrine sweat gland cell, sebaceous gland cells, type II pneumocytes, or any combination thereof.

Cells may comprise hormone-secreting cells including but not limited to anterior pituitary cells, intermediate pituitary cells, magnocellular neurosecretory cells, gut tract cells, respiratory tract cells, thyroid gland cells, parathyroid gland cells, adrenal gland cells, Leydig cells, theca interna cells, corpus luteum cells, juxtaglomerular cells, macula densa cells, peripolar cells, mesangial cells, pancreatic islet cells such as alpha cells, beta cells, delta cells, PP cells, and epsilon cells, or any combination thereof Cells may comprise epithelial cells including but not limited to keratinizing epithelial cells such as keratinocytes, basal cells, and hair shaft cells, stratified barrier epithelial cells such as surface epithelial cells of stratified squamous epithelium, basal cells of epithelia, and urinary epithelium cells, or any combination thereof.

Cells may comprise nerve cells or neurons including but not limited to sensory transducer cells, autonomic neuron cells, peripheral neuron supporting cells, central nervous system neurons such as interneurons, spindle neurons, pyramidal cells, stellate cells, astrocytes, oligodendrocytes, ependymal cells, glial cells, or any combination thereof.

Cells may comprise kidney cells including but not limited to, parietal cells, podocytes, mesangial cells, distal tubule cells, proximal tubule cells, Loop of Henle thin segment cells, collecting duct cells, interstitial kidney cells, or any combination thereof.

Cells may comprise pulmonary cells including, but not limited to type I pneumocyte, alveolar cells, capillary endothelial cells, alveolar macrophages, bronchial epithelial cells, bronchial smooth muscle cells, tracheal epithelial cells, small airway epithelial cells, or any combination thereof.

Cells may comprise extracellular matrix cells including, but not limited to epithelial cells, fibroblasts, pericytes, chondrocytes, osteoblasts, osteocytes, osteoprogenitor cells, stellate cells, hepatic stellate cells, or any combination thereof.

Cells may comprise muscle cells including, but not limited to skeletal muscle cells, cardiomyocytes, Purkinje fiber cells, smooth muscle cells, myoepithelial cells, or any combination thereof.

Cells may comprise muscle cells including, but not limited to skeletal muscle cells, cardiomyocytes, Purkinje fiber cells, smooth muscle cells, myoepithelial cells, or any combination thereof.

Cells may comprise blood cells and/or immune cells including, but not limited to erythrocytes, megakaryocytes, monocytes, macrophages, osteoclasts, dendritic cells, microglial cells, neutrophils, eosinophils, basophils, mast cells, T-cells, helper T-cells, suppressor T-cells, cytotoxic T-cells, natural killer T-cells, B-cells, natural killer (NK) cells, reticulocytes, or any combination thereof.

In some cases, the photo-emitter may comprise a chemiluminescent component, a photoluminescent component, a fluorescent molecule, a phosphorescent molecule, a luminescent molecule, a nanoparticle, a quantum dot particle, a microparticle, a histological stain, an immunofluorescent dye, a fluorescent dye, and a fluorescent protein.

In some cases a photo-emitter may be used to label cell nuclei. In some cases, a photo-emitter such as a live stain may be used to mark live cells. A live stain may be, for example, Calcein AM. In some examples a photo-emitter may be a dead stain used to mark dead cells. A dead stain may be, for example, Ethedium Homodimer (Eth-D1). The method may further comprise separating live cells. The method may further comprise separating dead cells.

In some cases, the photo-emitter may comprise a peptide, cell penetrating peptide, fluorescently-labeled peptide, intracellular probe, fluorescent probe, activity-based probe, fluorescent intracellular biosensor, fluorescent resonance energy transfer-based (FRET-based) reporter, and genetically modified fluorescent cell.

In some cases, the photoinitiator may comprise Eosin Y, erythrosine, rose Bengal, xanthone derivatives, triethanolamine, azobisisobutyronitrile (AIBN), benzoin derivatives, benziketals, hydroxyalkylphenones, acetophenone derivatives, trimethylolpropane triacrylate (TPT), acryloyl, chloride, benzoyl peroxide, camphorquinone, benzophenone, thioxanthones, and 2-hydroxy-1-[4-(hydroxyethoxy) phenyl]-2-methyl-1-propanone, 4-(2-hydroxyethylethoxy)-phenyl-(2-hydroxy-2-methyl propyl) ketone, 1-hydroxycyclohexyl-1-phenyl ketone and 2,2-dimethoxy-2-phenylacetophenone, and lithium phenyl-2,4,6-trimethylbenzoylphosphinate (LAP).

The method may comprise providing and/or using at least one polymeric precursor. Precursor may comprise collagen, gelatin, chitosan, polyethylene glycol (PEG), and polylactic-co-glycolic acid (PLGA), vinyl alcohol derivatives, vinylpyrrolidone derivatives, acrylate derivatives, methacrylate derivatives, and styrene derivatives.

The media chamber may further comprise a three-dimensional (3D) object that may not contain a photo-emitter. In some cases, the 3D object may contain a photo-emitter or a plurality of photo emitters. The medium may comprise more than one 3D object comprising a photo-emitter.

One or more than one 3D object(s) may comprise a photo-emitter that may not have overlapping excitation wavelengths with another 3D object comprising a photo-emitter.

In some cases, the photo-emitter may comprise a label. In some cases, the photo-emitter may comprise a tag, such as a fluorescent tag, a fluorophore, and/or a fluorogenic substrate.

The method may further comprise differentiating different 3D object types based on the formation of the polymer matrix from the at least one polymeric precursor.

The method may further comprise separating out from the medium any of the 3D objects without resultant encapsulation by the polymer matrix.

The separating out from the medium may comprise separation by physical size, separation by chemical binding, separation by electrostatic forces, separation by magnetic interactions, separation by mass, and separation by solubility. Separation techniques are not meant to be limiting.

Separation of cells may be based on a certain phenotype. Separation of cells may comprise separating cells with an upregulation of a certain biological event, such as an activity of a certain biochemical pathway or a component thereof in the cell. Various types of biosensors, fluorescent proteins, peptides, such as for example cell penetrating peptides, activity-based reporters, FRET reporters, enzyme reporters, biochemical reporters of different kinds, fluorescent beads, antibodies, nanoparticles, nanoparticle-based reporters, peptide-based reporters, and other biosensors or methods may be used to identify cells expressing a biological event. Such biological events may comprise for example the activity of a certain enzyme in the cell.

The methods may comprise providing a system for encapsulating three-dimensional (3D) objects. The system may comprise a media chamber configured to contain a medium comprising a three-dimensional (3D) object comprising a photo-emitter, at least one polymeric precursor, and a photoinitiator. The method may further comprise at least one energy source configured to apply a chemical stimulus or direct at least one energy beam to the media chamber; and one or more computer processors operatively coupled to the at least one energy source. The one or more computer processors may be individually or collectively programmed to apply the chemical stimulus or direct the at least one energy source to direct the at least one energy beam to the medium in the media chamber such that the ensuing reaction may induce the photo-emission from the photo-emitter. The photo-emitter may emit energy that may trigger the photoinitiator to initiate formation of the polymer matrix from the at least one polymeric precursor, which polymer matrix may at least partially encapsulate the 3D object.

The medium may further comprise a photoinhibitor that may prevent formation of the polymer matrix in one or more selected locations of the medium The system may comprise at least one energy beam comprising a single wavelength.

The system may comprise at least one energy beam comprising a plurality of wavelengths.

At least one energy beam may be selected from the group consisting of a laser, and a light emitting diode, arc lamp, incandescent, or fluorescent light source.

The method may comprise using a cell comprising the photo-emitter, a particle comprising the photo-emitter, a microparticle comprising the photo-emitter, a nanoparticle comprising the photo-emitter, or a surface comprising the photo-emitter Cells may be endothelial cells, fibroblasts, immune cells, keratinocytes, melanocytes, kidney cells, hepatocytes and cardiomyocytes.

The photo-emitter may be a chemiluminescent component, a photoluminescent component, a fluorescent molecule, a phosphorescent molecule, a luminescent molecule, a nanoparticle, a quantum dot particle, a microparticle, a histological stain, an immunofluorescent dye, a fluorescent dye, and/or a fluorescent protein.

The photo-emitter may be a photo-emitting peptide, a photo-emitting cell penetrating peptide, a photo-emitting intracellular probe, a photo-emitting reporter, and/or a photo-emitting activity-based reporter.

In some examples, the 3D object may comprise at least two photo-emitters.

In some examples, the 3D object may comprise a fluorescence resonance energy transfer (FRET) reporter.

The method may comprise using a photoinitiator. Photoinitiator may be Eosin Y, erythrosine, rose Bengal, xanthone derivatives, triethanolamine, azobisisobutyronitrile (AIBN), benzoin derivatives, benziketals, hydroxyalkylphenones, acetophenone derivatives, trimethylolpropane triacrylate (TPT), acryloyl, chloride, benzoyl peroxide, camphorquinone, benzophenone, thioxanthones, and 2-hydroxy-1-[4-(hydroxyethoxy)phenyl]-2-methyl-1-propanone, 4-(2-hydroxyethylethoxy)-phenyl-(2-hydroxy-2-methyl propyl) ketone, 1-hydroxycyclohexyl-1-phenyl ketone and 2,2-dimethoxy-2-phenylacetophenone and/or lithium phenyl-2,4,6-trimethylbenzoylphosphinate (LAP).

The method may comprise using at least a polymeric precursor. The polymeric precursor may be collagen, gelatin, chitosan, polyethylene glycol (PEG), polylactic-co-glycolic acid (PLGA), vinyl alcohol derivatives, vinylpyrrolidone derivatives, acrylate derivatives, methacrylate derivatives, styrene derivatives, or various combinations thereof.

The system may comprise a media chamber. The media chamber may comprise a three-dimensional (3D) object. In some cases, the 3D object may not contain a photo-emitter. In some cases, the 3D object may comprise more than one 3D object comprising a photo-emitter. In some cases, the method may comprise using more than one 3D object each comprising a photo-emitter that may not have overlapping excitation wavelengths with another 3D object comprising a photo-emitter.

The system may further comprise differentiating different 3D object types based on the formation of the polymer matrix from the at least one polymeric precursor without resultant encapsulation by the polymer matrix, including separation by physical size, chemical binding, electrostatic forces, magnetic interactions, mass, or solubility.

The present disclosure provides methods and systems for fluorescent-induced auto-encapsulation of 3D objects. In some cases, 3D objects may be biological material (e.g., living cells). In some examples, 3D objects may not be biological material.

The ability to select cells individually, or to select a set of cells of the same type from a larger population may be of great utility in healthcare, the pharmaceutical industry, and basic research. However, current methods, including FACS, may do so with the use of shear forces, and may suffer from a trade-off between throughput and the shear forces experienced by the sorted cells. That is, higher sorting throughput rates may only be possible when correspondingly high shear forces are applied to cells during the sorting process. In some cases, these forces can disrupt cell function, and in the extreme case may lead to cell death. A potential solution to the issues of single cell encapsulation techniques may be achieved with high throughput cell encapsulation without exerting large shear forces on the cells. Provided herein are methods and systems comprising selective encapsulation of cells upon exposure to an energy source (e.g., a laser). The methods of the present disclosure may facilitate selective encapsulation of 3D objects, such as biological 3D objects, for example cell. The methods may not comprise the use of shear force. Not using shear force may contribute to cell viability and integrity among other advantages.

In some cases, the method comprises labeling a specific cell or a specific cell type in a larger cell population with a fluorescent protein or molecule. Non-limiting examples of the cell types that can be encapsulated include endothelial cells, fibroblasts, immune cells, keratinocytes, melanocytes, kidney cells, hepatocytes, and cardiomyocytes.

Non-limiting examples of the fluorescent protein or molecule include fluorescently labeled antibodies (e.g., FITC-conjugated immunoglobulin (IgG)), and fluorescent dyes (e.g., boron-dipyrromethene, fluorescein, lissamine rhodamine B, green fluorescent protein (GFP)).

In some cases, the methods may comprise immersing the cells in a bio-compatible medium which may be sensitized to the fluorescent emission of the labelled cells using a photoinitiator, such that exposure to that light may cause the material to polymerize, gel, and/or solidify. The bio-compatible medium may comprise at least one photoinitiator. In some cases the photoinitiator may be Eosin Y (EY) or triethanolamine (TEA). EY and TEA, when combined may polymerize in response to exposure to visible light (e.g., wavelengths of about 390 to 700 nanometers). Non-limiting examples of photoinitiators include azobisisobutyronitrile (AIBN), benzoin derivatives, benziketals, hydroxyalkylphenones, acetophenone derivatives, trimethylolpropane triacrylate (TPT), acryloyl chloride, benzoyl peroxide, camphorquinone, benzophenone, thioxanthones, and 2-hydroxy-1-[4-(hydroxyethoxy)phenyl]-2-methyl-1-propanone.

Hydroxyalkylphenones may include 4-(2-hydroxyethylethoxy)-phenyl-(2-hydroxy-2-methyl propyl) ketone (Irgacure® 295), 1-hidroxycyclohexyl-1-phenyl ketone (Irgacure® 184) and 2,2-dimethoxy-2-phenylacetophenone (Irgacure® 651). Acetophenone derivatives may include 2,2-dimethoxy-2-phenylacetophenone (DMPA). Thioxanthones may include isopropyl thioxanthone. The bio-compatible medium may comprise at least one polymeric precursor. Non-limiting examples of polymeric precursors include collagen, chitosan, polyethylene glycol (PEG), and polylactic-co-glycolic acid (PLGA), gelatin, and alginate. The bio-compatible medium may comprise at least one polymeric precursor. Non-limiting examples of polymeric precursors include collagen, chitosan, polyethylene glycol (PEG), and polylactic-co-glycolic acid (PLGA). Polymeric precursors may include inert or reactive organic compounds that self-assemble with exposure to the wavelength emitted by the entity of interest. The entity of interest may be, for example, a cell.

The method may comprise exposing the cell-laden medium to an energy source which may overlap in wavelength with the absorption band of the fluorescent label, but may not overlap in wavelength with that of the sensitized encapsulation medium. In some cases, the exposed energy may at least partially overlap in wavelength with that of the sensitized encapsulation medium. In some cases, such overlap may be undesired.

In some cases, the energy source may be a plurality of energy sources. The plurality of energy sources may direct at least one energy beam. The plurality of energy sources may apply a chemical stimulus to the media chamber. The at least one energy beam may be or may include coherent light. In some cases, the at least one energy beam is a laser beam. The energy source may be a laser. In some examples, the laser may be a fiber laser. For example, a fiber laser may be a laser with an active gain medium that includes an optical fiber doped with rare-earth elements, such as, for example, erbium, ytterbium, neodymium, dysprosium, praseodymium, thulium and/or holmium.

The energy source may be a short-pulsed laser. The energy source may be a femto-second pulsed laser. The femtosecond pulsed laser may have a pulse width less than or equal to about 500 femtoseconds (fs), about 250 fs, about 240 fs, about 230 fs, about 220 fs, about 210 fs, about 200 fs, about 150 fs, about 100 fs, about 50 fs, about 40 fs, about 30 fs, about 20 fs, about 10 fs, about 9 fs, about 8 fs, about 7 fs, about 6 fs, about 5 fs, about 4 fs, about 3 fs, about 2 fs, about 1 fs, or less. The femtosecond pulsed laser may be, for example, a titanium:sapphire (Ti:Sa) laser. The at least one energy source may be derived from a coherent light source.

The energy source can be a lamp, a spectrally filtered lamp, and light emitting diode or other solid state-lighting device, and a laser or any laser-type device such as, but not limited to, an optical parametric oscillator or optical parametric amplifier. The energy beam may be a continuous energy wave. The energy beam may be a pulsed energy wave. The energy source may be a narrow wavelength. The energy source may be broader in spectrum.

The energy source (e.g., laser) may provide an energy beam (e.g., light beam) having a wavelength from e.g. about at least 300 nm to about 5 mm or more. The energy source (e.g., laser) may provide energy (e.g., laser beam) having a wavelength of about at least 600 to about 1500 nm or more. The energy source (e.g., laser) may provide energy (e.g., laser beam) having a wavelength from about at least 350 nm to about 1800 nm or more. The energy source (e.g., laser) may provide energy (e.g., laser beam) having a wavelength from about at least 1800 nm to about 5 mm or more. The energy source (e.g., laser) may provide energy (e.g., laser beam) having a wavelength of about 300 nm. The energy source (e.g., laser) may provide energy (e.g., laser beam) having a wavelength of about 400 nm. The energy source (e.g., laser) may provide energy (e.g., laser beam) having a wavelength of about 600 nm. The energy source (e.g., laser) may provide energy (e.g., laser beam) having a wavelength of about 700 nm. The energy source (e.g., laser) may provide energy (e.g., laser beam) having a wavelength of about 800 nm. The energy source (e.g., laser) may provide energy (e.g., laser beam) having a wavelength of about 900 nm. The energy source (e.g., laser) may provide energy (e.g., laser beam) having a wavelength of about 1000 nm. The energy source (e.g., laser) may provide energy (e.g., laser beam) having a wavelength of about 1100 nm. The energy source (e.g., laser) may provide energy (e.g., laser beam) having a wavelength of about 1200 nm. The energy source (e.g., laser) may provide energy (e.g., laser beam) having a wavelength of about 1300 nm. The energy source (e.g., laser) may provide energy (e.g., laser beam) having a wavelength of about 1400 nm. The energy source (e.g., laser) may provide energy (e.g., laser beam) having a wavelength of about 1500 nm. The energy source (e.g., laser) may provide energy (e.g., laser beam) having a wavelength of about 1600 nm. The energy source (e.g., laser) may provide energy (e.g., laser beam) having a wavelength of about 1700 nm. The energy source (e.g., laser) may provide energy (e.g., laser beam) having a wavelength of about 1800 nm. The energy source (e.g., laser) may provide energy (e.g., laser beam) having a wavelength of about 1900 nm. The energy source (e.g., laser) may provide energy (e.g., laser beam) having a wavelength of about 2000 nm. The energy source (e.g., laser) may provide energy (e.g., laser beam) having a wavelength of about 3000 nm. The energy source (e.g., laser) may provide energy (e.g., laser beam) having a wavelength of about 4000 nm. The energy source (e.g., laser) may provide energy (e.g., laser beam) having a wavelength of about 5000 nm.

The absorption band of the fluorescent label may have a wavelength of about 300 nm to about 5000 nm. The absorption band of the medium may have a wavelength of about 300 nm to about 5000 nm.

The encapsulation medium and the photo-emitters (e.g., fluorescent labels) may be chosen so that it may be possible to optically excite the label without inducing appreciable absorption in the encapsulation medium. By doing so, the undesirable whole-scale gelling of the medium may be prevented when the cell-laden medium is exposed to the chemical stimulus (e.g. energy source and/or excitation light).

During the exposure to the chemical stimulus applied, such as excitation light, the incident light may be absorbed by the photo-emitters in or on the 3D object. The chemical stimulus or light may be re-emitted with some Stokes shift in the physical/chemical properties of the chemical stimulus applied, such as a fluorescence band. The re-emitted chemical stimulus may be emitted in full solid angle around the 3D object that may not comprise any directionality. For example, fluorescence may be emitted in the full solid angle around the 3D object (for example a cell or a particle) without any directionality. Alternatively, in some cases, the re-emitted chemical stimulus may be emitted in full solid angle around the 3D object that may comprise a certain directionality The method may further comprise initiating a photo-polymerization reaction in the medium. In some cases, the photo-polymerization reaction may be initiated to surround the 3D object (in some cases a cell). The photo-polymerization may be initiated by the absorption of the emitted light of the photo-emitter that may be comprised in the 3D object by the photo-initiator present in the encapsulation medium. For example, the photo-polymerization may be initiated by the absorption of the fluorescence of the photo-emitter (such as a fluorescent label or any other type of photo-emitting particle, substance, protein or other material) that may be located on or within an example plurality of cells by the photo-initiator present in the encapsulation medium.

This photo-polymerization may be selective. Selective photo-polymerization may result in selective encapsulation of a plurality of 3D objects with a common feature or characteristic. In an example, fluorescently labelled cells comprising a specific label designed for a desired purpose (and only the fluorescently labeled cells) may be encapsulated in polymerized partitions. Polymerized partitions may have different shapes. For example, polymerized partitions may be polymerized spheres.

The photo-initiation due to the applied chemical stimulus (for example fluorescence) and the polymerization itself may be localized to the area immediately surrounding a desired 3D object (such as a cell). The localized intensity of the chemical stimulus (i.e., the fluorescence intensity coming from an example 3D object, such as a cell) may cause the photo-polymerization to be localized.

The chemical stimulus (such as an energy, a fluorescence or other type of stimulus) may spread out in three dimensions after being emitted. For example, the stimulus (for example light, such as fluorescence) may spread out in three dimensions after being emitted. As such, the intensity may fall off at increasing distance from the 3D object (for example a cell). In addition, the encapsulation medium may absorb the chemical stimulus (such as fluorescence) as it passes through it.

Figure 1B:
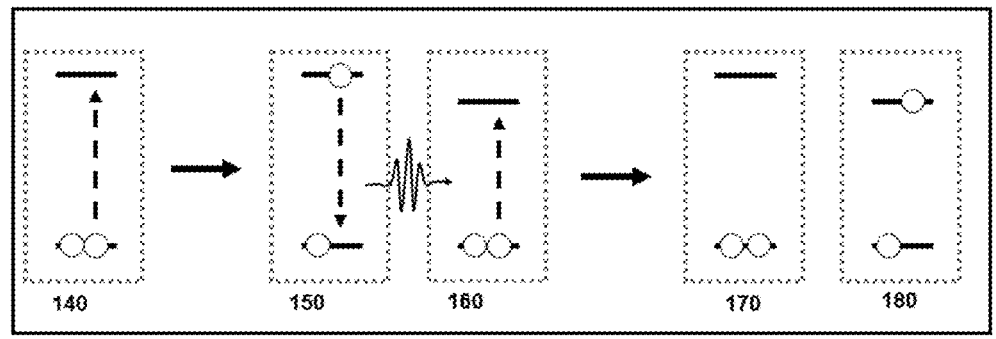
FIG. 1B schematically represents a simplified Jablonski diagram of the electronic state involved in an example photoactivation process.

FIG. 1A and FIG. 1B provide an example of the cell encapsulation methods provided herein. For example, FIG. 1A schematically represents the cell encapsulation process and an example apparatus. As shown in FIG. 1A, a fluorescently labeled cell 110 may be immersed in a photosensitive medium in an enclosure 100. The enclosure may be for example, a microscope slide, a cover glass, a microfluidic device, chip, or other enclosure. The system may be illuminated (200) from the top side with a wavelength of light that may be transmitted by the photosensitive medium and absorbed by the an example photo-emitter comprised in the cells, such as a fluorescent tag, biosensor, fluorescent reporter, nanoparticle, or other type of photo-emitter. Alternatively, another type of chemical stimulus may be applied. The photo-emitter may emit light (for example fluoresce at a wavelength) that may be absorbed by the photo-initiator in the photosensitive medium. This may initiate the photo-polymerization reaction within the medium, thereby encapsulating the cell comprising the photo-emitter. It should be noted that a cell may used here only as an example. The method may be performed on 3D objects other than cells which may not be living. In other examples, different types of living creatures such as tissues, cells, bacteria, fungi, or other 3D objects may be used to perform the methods.

FIG. 1B schematically represents a simplified Jablonski diagram of the electronic state involved in an example photoactivation process. The photoactivation process may occur with one, two, or multi-photon laser-based illumination or illumination at a given wavelength using a non-coherent laser system. Alternatively, another type of chemical stimulus may be applied. For example, the chemical stimulus may be applying heat energy or other types of energy. In an example, the illumination may be absorbed by a photo-emitting 3D object (140, 150, and 170) such as a cell-tagging fluorophore, a cell comprising a photo-emitter, a photo-emitter not comprising a cell, or other 3D object. In this example, the energy (such as fluorescence) is absorbed which may be due to the Stoke's shift being resonant with the photoinitiator absorption band. The photo-initiator (160 and 180) to which the chemical stimulus is applied (for example, is excited by light exposure) may initiate the polymerization reaction.

In some cases, the methods and systems provided herein may achieve high throughput fluorescent-induced auto-encapsulation. In some examples, the cross-section of the exposure area may be large (e.g., preferably the size of the encapsulation medium itself), enabling exposure of a large volume in one shot. The method may comprise an excitation exposure wavelength that matches the excitation band of the fluorescent label while not significantly overlapping with the excitation band of the photo-initiator. Furthermore, the method may comprise controlling the size of the encapsulated sphere (e.g., cell) by changing the exposure parameters. For example, increasing the exposure length or the exposure intensity may generate larger spheres (i.e., that can encapsulate cells with a diameter of about 1000 μm), while decreasing the exposure length or intensity may generate smaller spheres i.e., that may encapsulate cells with a diameter of about 100 μm.

Next, the method comprises sorting of the cells into multiple "bins." Multiple fluorescent proteins/molecules with non-overlapping excitation wavelengths may enable sorting of the cells into multiple 'bins'. The method for preferred multi-bin sorting may comprise fluorescent labels with fluorescence spectra that are overlapping, while their excitation spectra are non-overlapping. Next, the method may comprise using multiple exposure sources to selectively encapsulate differently labeled cells by mechanically separating the encapsulated cells from the un-encapsulated cells after each exposure. As an alternative, the different exposures (corresponding to the different labels) may be chosen so that the encapsulated spheres in each case are of different sizes. In some cases, all exposures may be done in succession. In other cases, all exposures may be done simultaneously. Next, the method may comprise differentiating the different cell types based upon the size of their encapsulating sphere.

In some cases, the methods provided herein may comprise a medium that does not comprise a photoinitiator. In such cases, the methods provided herein may rely on a heat-based polymerization for auto-encapsulation. In this case, the encapsulation medium may have some temperature threshold at which it polymerizes. The medium may be chosen so that this temperature is compatible with living cells. In this example, the method may comprise the steps as described elsewhere herein, with the exception of not needing the excitation wavelength of the fluorophore to be non-overlapping with the photo-initiator absorption (due to the lack of photoinitiator). When excitation light is absorbed, some of the energy may be emitted into the encapsulation as heat. The generation of localized heat may be due to the Stokes shift between excitation and emission. The generation of localized heat may be due to the quantum yield being less than unity. The localized heat may heat the full solid angle around the cell in a non-directional manner. The exposure time and intensity may be chosen so that the temperature of the volume around the cell exceeds the temperature threshold of the medium thus, encapsulating the cell in a sphere.

Figure 2:
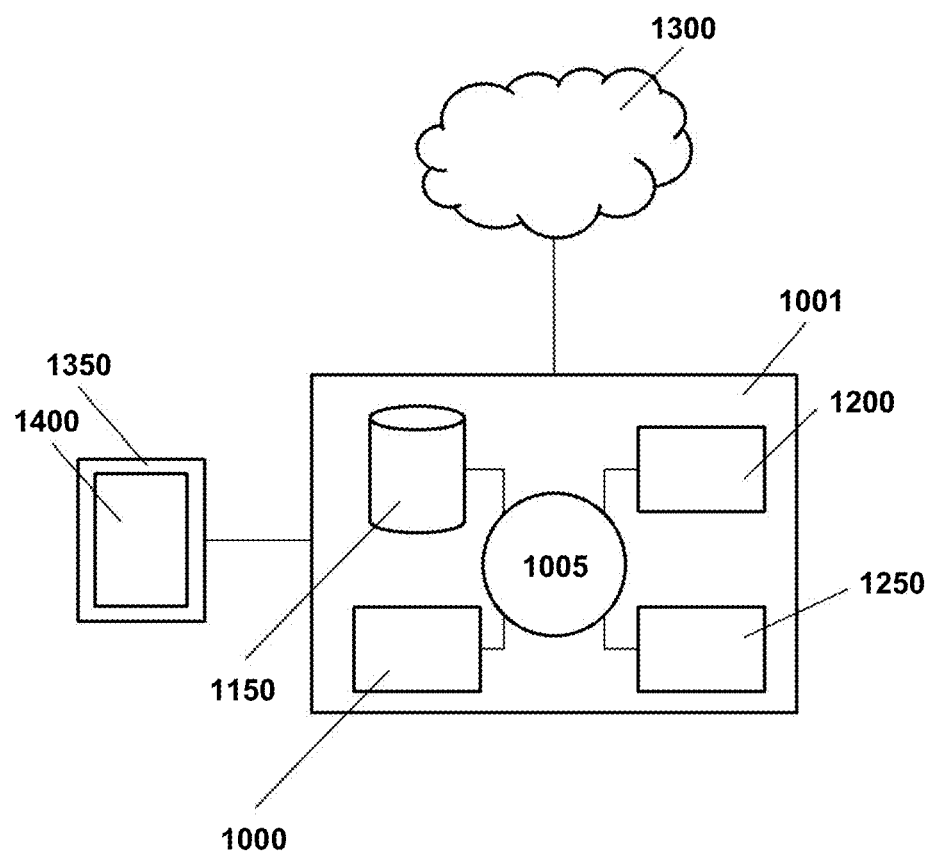
FIG. 2 shows a computer system that is programmed or otherwise configured to implement the methods provided herein.

The present disclosure provides computer systems that are programmed to implement methods of the disclosure. FIG. 2 shows a computer system 1001 that is programmed or otherwise configured to perform the methods of the present disclosure. For example, the computer may be programmed or otherwise configured to apply a chemical stimulus to a medium. The computer system 1001 can regulate various aspects of the methods of the present disclosure. For example, the computer systems can regulate various aspects of auto-encapsulation of 3D objects. For example, the methods may comprise determining the size of an encapsulating sphere based on control of exposure parameters. The computer system 1001 can be an electronic device of a user or a computer system that is remotely located with respect to the electronic device. The electronic device can be a mobile electronic device.

The computer system 1001 includes a central processing unit (CPU, also "processor" and "computer processor" herein) 1005, which can be a single core or multi core processor, or a plurality of processors for parallel processing. The computer system 1001 also includes memory or memory location 1100 (e.g., random-access memory, read-only memory, flash memory), electronic storage unit 1150 (e.g., hard disk), communication interface 1200 (e.g., network adapter) for communicating with one or more other systems, and peripheral devices 1250, such as cache, other memory, data storage and/or electronic display adapters. The memory 1100, storage unit 1150, interface 1200 and peripheral devices 1250 are in communication with the CPU 1005 through a communication bus (solid lines), such as a motherboard. The storage unit 1150 can be a data storage unit (or data repository) for storing data. The computer system 1001 can be operatively coupled to a computer network ("network") 1300 with the aid of the communication interface 1200. The network 1300 can be the Internet, an internet and/or extranet, or an intranet and/or extranet that is in communication with the Internet. The network 1300 in some cases is a telecommunication and/or data network. The network 1300 can include one or more computer servers, which can enable distributed computing, such as cloud computing. The network 1300, in some cases with the aid of the computer system 1001, can implement a peer-to-peer network, which may enable devices coupled to the computer system 1001 to behave as a client or a server.

The computer system 1001 includes a central processing unit (CPU, also "processor" and "computer processor" herein) 1005, which can be a single core or multi core processor, or a plurality of processors for parallel processing. The computer system 1001 also includes memory or memory location 1100 (e.g., random-access memory, read-only memory, flash memory), electronic storage unit 1150 (e.g., hard disk), communication interface 1200 (e.g., network adapter) for communicating with one or more other systems, and peripheral devices 1250, such as cache, other memory, data storage and/or electronic display adapters. The memory 1100, storage unit 1150, interface 1200 and peripheral devices 1250 are in communication with the CPU 1005 through a communication bus (solid lines), such as a motherboard. The storage unit 1150 can be a data storage unit (or data repository) for storing data. The computer system 1001 can be operatively coupled to a computer network ("network") 1300 with the aid of the communication interface 1200. The network 1300 can be the Internet, an internet and/or extranet, or an intranet and/or extranet that is in communication with the Internet. The network 1300 in some cases is a telecommunication and/or data network. The network 1300 can include one or more computer servers, which can enable distributed computing, such as cloud computing. The network 1300, in some cases with the aid of the computer system 1001, can implement a peer-to-peer network, which may enable devices coupled to the computer system 1001 to behave as a client or a server.

The CPU 1005 can execute a sequence of machine-readable instructions, which can be embodied in a program or software. The instructions may be stored in a memory location, such as the memory 1100. The instructions can be directed to the CPU 1005, which can subsequently program or otherwise configure the CPU 1005 to implement methods of the present disclosure. Examples of operations performed by the CPU 1005 can include fetch, decode, execute, and write back.

The CPU 1005 can be part of a circuit, such as an integrated circuit. One or more other components of the system 1001 can be included in the circuit. In some cases, the circuit is an application specific integrated circuit (ASIC).

The storage unit 1150 can store files, such as drivers, libraries and saved programs. The storage unit 1150 can store user data, e.g., user preferences and user programs. The computer system 1001 in some cases can include one or more additional data storage units that are external to the computer system 1001, such as located on a remote server that is in communication with the computer system 1001 through an intranet or the Internet.

The computer system 1001 can communicate with one or more remote computer systems through the network 1300. For instance, the computer system 1001 can communicate with a remote computer system of a user (e.g., a scientist or technician). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1001 via the network 1300.

Methods as described herein can be implemented by way of machine (e.g., computer processor) executable code stored on an electronic storage location of the computer system 1001, such as, for example, on the memory 1100 or electronic storage unit 1150. The machine executable or machine readable code can be provided in the form of software. During use, the code can be executed by the processor 1005. In some cases, the code can be retrieved from the storage unit 1150 and stored on the memory 1100 for ready access by the processor 1005. In some situations, the electronic storage unit 1150 can be precluded, and machine-executable instructions are stored on memory 1100.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1350 that comprises a user interface (UI) 1400 for providing, for example for example, an image of the complex structure to be processed by the methods disclosed herein. Examples of UI's include, without limitation, a graphical user interface (GUI) and web-based user interface. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1005. The algorithm can, for example, sort 3D objects based on defined characteristics. For example, the algorithm may sort cell types based on encapsulation sphere size and/or the presence or absence of fluorescence at a specific wavelength or the intensity thereof.

FIG. 3 shows example formulations of example chemicals that may be used in a resin in the methods described herein. The table presented in FIG. 3 includes the name of the chemicals used as an example material (resin), full names of the same chemicals, lot number, manufacturer, concentration used, amount used for making 1455 μl of the example material (resin). The Eosin Y concentration may depend on the structure to be printed and its amount may ranges from 15 μl to 60 μl for making 1455 μl of the example material (resin). In some cases, the amount of Eosin Y may be within the range of 23 to 45 μl for making 1455 μl of the example material (resin). The formulation provided in FIG. 3 as well as formulations provided in other figures are only provided as examples and are not meant to be limiting. Various other chemicals at various ratios may be added to alter the chemistry. The chemistry of the materials used to perform the methods of the present disclosure may be optimized for desired purposes. For example, chemistry may be altered to adjust properties such as stiffness, porosity, permeability, and other characteristics of the material.

Figures 4, 5:
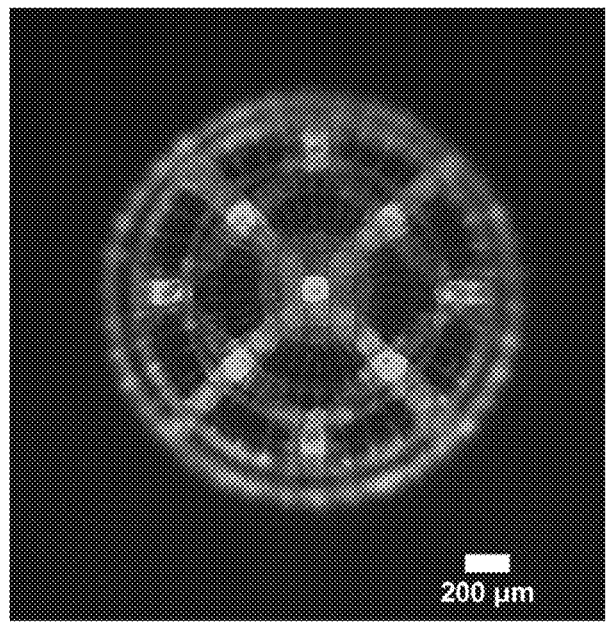
FIG. 4 shows an example of incorporating N-vinylpyrrolidone (NVP) in an example resin that may be used in the methods of the present disclosure.
FIG. 5 show the effect of incorporating N-vinylpyrrolidone in an example three-dimensional (3D) printing process.

FIG. 4 shows an example of incorporating 1-Vinyl-2-pyrrolidinone (NVP) in an example resin that may be used in the methods of the present disclosure and its corresponding effects on the speed of an example 3D printing process. In some cases, incorporation of 1-Vinyl-2-pyrrolidinone (NVP) into the formulation of example resins may increase the print speed. NVP may be a water-soluble co-monomer which may reduce the oxygen inhabitation time. This may increase the rate of polymerization. FIG. 4 shows the printing time for an example 3D structure basket (shown in FIG. 5) with 1 vol % NVP in the formulation of the resin vs control sample with no NVP. The exposure frequency (EF) may be one of the parameters that may affect the speed of printing. The control experiment EF was set for 30 Hz. In some examples of performing the methods of the present disclosure, the results showed that when the EF increased from 30 Hz to 40 Hz nothing was printed with the formulation reported in FIG. 4. In this example, incorporation of 1% NVP allowed to print at EF=40 Hz. That reduced the print time for a basket from 79 min to 57 min (27.8% faster printing).

FIG. 5 shows an example basket that may be printed using the methods of the present disclosure. In an experiment, this example basket was printed using a resin with the formulations presented in FIG. 3 and FIG. 4 with the formulation including 1 vol % NVP. In this example, all fine features were printed properly. Number of the samples=6.

In an example, 1 vol % NVP was directly added to a 150K HUVECs cells media. After 48 hrs cells were treated with Trypan blue to be analyzed using the live/dead assay. The results showed that >98% of the HUVECs cells were alive. These results illustrated that 1 vol % NVP may not be toxic to the HUVECs cells and may increase the print speed by about 10%.

In some examples, adding 1 vol % NVP to the formulation of the resin may increase the print speed by at least about 10%, 15%, 20%, 25%, 27%, 30%, 40%, 50%, or more. In some examples, adding 1 vol % NVP to the formulation of the resin may increase the print speed by at most about 90%, 80%, 70%, 60%, 50%, 40%, 30%, 28%, 27%, 25%, 20%, 15%, 10%, or less.

In some cases, incorporation of Pentaerythritol Triacrylate (PETA) and Pentaerythritol Tetracrylate may change the mechanical properties (such as stiffness, porosity, permeability, or other properties) of UV cured structures. PETA may be used as a crosslinker with three acrylate crosslinking groups that may bond with three different strands of polyethylene glycol diacrylate (PEGDA). The structures made with PETA may be more rigid.

Figure 6A:
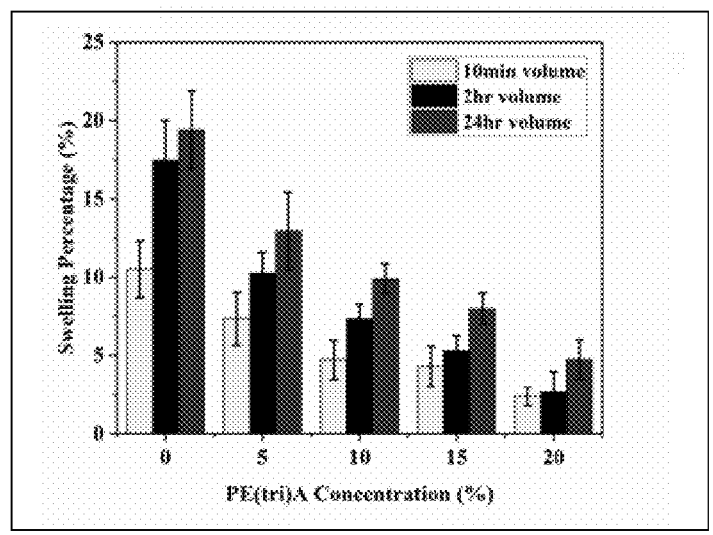
FIG. 6A shows an example where the swelling ratio (based on volume percent) of the three-dimensional (3D) structure may be affected by a select component of an example resin.

FIG. 6A shows an example where the swelling ratio (based on volume percent) of the 3D structure may be affected by a select component of an example resin.

Figure 6B:
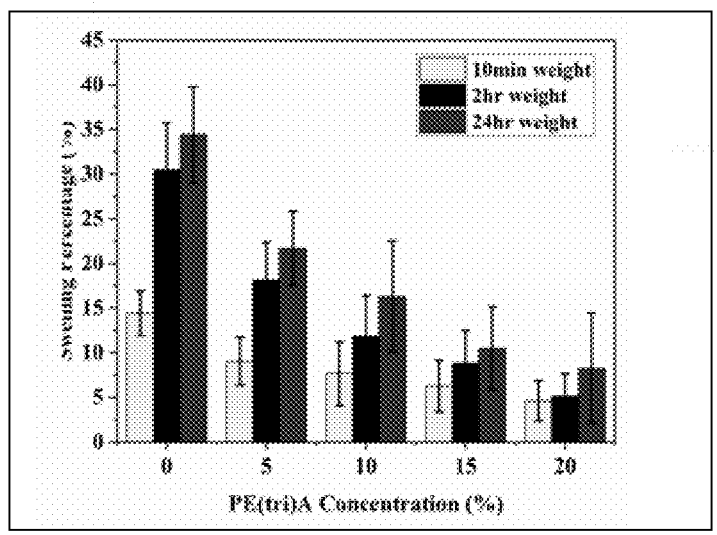
FIG. 6B shows an example where the swelling ratio (based on weight percent) of the three-dimensional (3D) structure may be affected by a select component of an example resin.

FIG. 6B shows an example where the swelling ratio (based on weight percent) of the 3D structure may be affected by a select component of an example resin.

To show the mechanical properties of PETA incorporated 3D structures, an example swelling test was performed on hollow tube structures. When hollow tubes were soaked into the 1× phosphate buffered saline (PBS), the amount of water uptake (based on weight) and change in size (based on volume) were measured after 10 min, 2 hrs and 24 hrs of soaking. FIGS. 6A and 6B show the swelling percentage of 3D structure tube as a function of PETA concentration for volume and weight, respectively. FIG. 6A shows that incorporation of PETA up to 20 vol % reduced the volume swelling ratio from 19.4±2.5% to 4.7±1.3% after 24 hrs in 1×PBS. FIG. 6B shows that in this particular example, incorporation of PETA for up to 20 vol % reduced the swelling percentage weight from 34.4±5.4% to 8.3±6.2% after 24 hrs in 1×PBS. These results may suggest that incorporation of PETA may alter mechanical properties of the 3D structures (such as stiffness). In this example lesser amounts of water molecules penetrated into the polymer chains and therefore less amount of swelling was observed.

Such modifications to the chemistry of the resins to be used in the method of the present disclosure may be purposefully made to optimize the methods and systems for different applications. For example, should long term cell culture in the biocompatible material be desired, chemistry may be adjusted to increase the porosity and permeability of the structure to allow for a better mass transfer to the growing cells. For example, media comprising cell nutrients may be more easily delivered to the cells. In some examples, reagents may be delivered to the cells. In some examples reagents delivered to the cells may comprise photo-emitters. In some examples, chemistry may be adjusted to allow for the transfer of certain photo-emitters through the material at a certain time point during an example experiment or procedure (mid-experiment for example). Various physical properties such as stiffness may be desired to perform such examples. Material (resin) chemistry may be adjusted accordingly.

Long-term culture of cells in the biocompatible material may comprise growing cells in the material for several hours to several weeks. This may further comprise performing various types of experiments on the cells. In some examples, tumor spheroids may be generated. For example, tumor spheroids may be generated to study cells in a biologically relevant micro-environment, for example, breast cancer micro-environments. Such experiments may be performed to mimic conditions in-vivo.

EXAMPLES

Example 1—Bulk Cell Encapsulation

A bulk encapsulation of cells is performed using the methods and systems provided herein. The cells are immersed in a medium comprising a at least one photoinitiator and at least one polymer precursor. The medium is reactive to the fluorophore emission but not to the incoming excitation wavelength.

Example 2—Single Cell Encapsulation

A single cell encapsulation that allows for separation from cells that are not encapsulated by light exposure is performed using the methods and systems provided herein. Cells that are not encapsulated are non-fluorescent or have a fluorophore present but are either: 1) not reactive to the wavelength of light used or 2) the fluorescent emission is non-reactive with the photopolymer in the media.

Example 3—Encapsulation of Cells Based on Expression of Fluorophores

Encapsulation of cells based on expression levels of fluorophore is performed using the methods and systems provided herein. The cells comprising a low level expression are not be encapsulated. On the other hand, high-expressing cells (i.e., cells expressing the fluorophore at a intensity) are encapsulated due to intensity of the fluorescent label.

In an example, the methods and systems comprise a light source that cells of interest are reactive to while in a medium that reacts to the fluorescent emission of the labeled cells. In this case, a localized directionless light-induced polymerization can cause auto- or self-encapsulation of a given cell population. Using a light source cells can rapidly and deterministically be encapsulated with a shear force-free method. Encapsulated cells can then be isolated in bulk from cells that are not encapsulated. The method and systems provided herein comprise large scale cell encapsulation, isolation, and or sorting without the use of shear forces.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for at least partially encapsulating a three-dimensional (3D) object, comprising
    (a) providing a media chamber comprising a medium comprising (i) said 3D object comprising a photo-emitter, wherein said 3D object is a biological material, (ii) at least one polymeric precursor, and (iii) a photoinitiator; and
    (b) directing at least one energy beam to said medium in said media chamber to induce photo-emission from said photo-emitter wherein said photo-emitter emits energy that triggers said photoinitiator to initiate formation of a polymer matrix from said at least one polymeric precursor, which polymer matrix at least partially encapsulates said 3D object.

2. The method of claim 1, wherein said photo-emitter comprises one or more emissive components.

3. The method of claim 2, wherein said photo-emitter is a fluorescent polymer sphere.

4. The method of claim 2, wherein said photo-emitter is a cell-containing emissive nanoparticle.

5. The method of claim 1, wherein said medium further comprises a photoinhibitor that prevents formation of said polymer matrix in one or more selected locations of said medium.

6. The method of claim 1, wherein said at least one energy beam comprises a single wavelength.

7. The method of claim 1, further comprising using a full spectrum illumination with distinct wavelength bands blocked.

8. The method of claim 1, further comprising using a full spectrum illumination.

9. The method of claim 1, wherein said at least one energy beam is selected from the group consisting of a laser, a light emitting diode, an arc lamp, an incandescent light source, and a fluorescent light source.

10. The method of claim 1, wherein said 3D object comprises a cell.

11. The method of claim 10, wherein said cell is selected from the group consisting of an endothelial cell, a fibroblast, an immune cell, a keratinocyte, a melanocyte, a kidney cell, a hepatocyte, and a cardiomyocyte.

12. The method of claim 1, wherein said photo-emitter is selected from the group consisting of a chemiluminescent component, a photoluminescent component, a fluorescent molecule, a phosphorescent molecule, a luminescent molecule, a nanoparticle, a quantum dot particle, a microparticle, a histological stain, an immunofluorescent dye, a fluorescent dye, a fluorescent protein, a photo-emitting peptide, a photo-emitting cell penetrating peptide, a photo-emitting intracellular probe, a photo-emitting reporter, and a photo-emitting activity-based reporter.

13. The method of claim 1, wherein said 3D object comprises at least two photo-emitters.

14. The method of claim 13, wherein said 3D object comprises a fluorescent resonance energy transfer (FRET) reporter.

15. The method of claim 1, wherein said photoinitiator is selected from the group consisting of Eosin Y, erythrosine, rose Bengal, xanthone derivatives, triethanolamine, azobisisobutyronitrile (AIBN), benzoin derivatives, benziketals, hydroxyalkylphenone, acetophenone derivatives, trimethylopropane triacrylate (TPT), acryloyl chloride, benzoyl peroxide, camphorquinone, benzophenone, thioxanthones, and 2-hydroxy-1-[4-(hydroxyethoxy)phenyl]-2-methyl-1-propanone, 4-(2-hydroxyethylethoxy)-phenyl-(2-hydoxy-2-methyl propyl) ketone, 1-hydroxycyclohexyl-1-phenyl ketone and 2,2-dimethoxy-2-phenylacetophenone, and lithium phenyl-2,4,6-trimethylbenzolphosphinate (LAP).

16. The method of claim 1, wherein said at least one polymeric precursor is selected from the group consisting of collagen, gelatin, chitosan, polyethylene glycol (PEG), polylactic-co-glycolic acid (PLGA), vinyl alcohol derivatives, vinylpyrrolidone derivatives, acrylate derivatives, methacrylate derivatives, and styrene derivatives.

17. The method of claim 1, wherein said media chamber further comprises a second three-dimensional (3D) object, wherein said second 3D object does not contain a photo-emitter.

18. The method of claim 1, wherein said medium comprises more than one 3D object comprising a photo-emitter.

19. The method of claim 18, wherein said more than one 3D object comprises a photo-emitter that does not have overlapping excitation wavelengths with another 3D object comprising a photo-emitter.

20. The method of claim 1, further comprising differentiating different 3D object types based on the formation of said polymer matrix from said at least one polymeric precursor.

\* \* \* \* \*